(12) United States Patent
Fauveau et al.

(10) Patent No.: US 7,192,920 B2
(45) Date of Patent: *Mar. 20, 2007

(54) DERIVATIVES OF ECHINOCANDINE, THEIR PREPARATION PROCESS AND THEIR USE AS ANTIFUNGALS

(75) Inventors: Patrick Fauveau, Livry Gargan (FR); Stephen Hawser, Arbizzano Di Valpolicella (IT); Gilles Lebourg, Gagny (FR); Laurent Schio, Bondy (FR)

(73) Assignee: Aventis Pharma SA (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/225,627

(22) Filed: Sep. 13, 2005

(65) Prior Publication Data

US 2006/0035820 A1    Feb. 16, 2006

Related U.S. Application Data

(62) Division of application No. 10/018,073, filed as application No. PCT/FR00/01568 on Jun. 8, 2000, now Pat. No. 7,022,669.

(30) Foreign Application Priority Data

Jun. 9, 1999    (FR) .................................. 99 07251

(51) Int. Cl.
*A61K 38/12*    (2006.01)
(52) U.S. Cl. ................. 514/9; 514/2; 514/11; 530/317; 530/318; 530/300; 530/333; 424/9.1; 930/270
(58) Field of Classification Search .............. 514/9, 514/11, 2; 530/317, 318, 300, 333; 930/270; 424/9.1
See application file for complete search history.

(56) References Cited

U.S. PATENT DOCUMENTS 6,677,429 B1 *   1/2004   Courtin et al. .............. 530/317
7,005,417 B1 *   2/2006   Corbier et al. ............. 530/317

FOREIGN PATENT DOCUMENTS

WO    WO 96/13272   *   5/1996
WO    WO 99/29716   *   6/1999

* cited by examiner

Primary Examiner—Chih-Min Kam
(74) Attorney, Agent, or Firm—Charles A. Muserlian

(57) ABSTRACT

A subject of the invention, in all possible isomer forms as well as their mixtures, is the compounds of formula (I):

in which
either $R_1$: H or $CH_3$ and
$R_2$: cyclohexyl substituted by an amine, a $(CH_2)b\text{-}C\equiv N$ radical or $R_1$ and $R_2$ together with the nitrogen which carries them form a ring with 3, 4 or 5 carbons optionally substituted by an amine
$R_3$: hydrogen, methyl or hydroxyl
$R_4$: hydrogen or hydroxyl
R: represents a linear, branched or cyclic chain
T: hydrogen, methyl, $CH_2CONH_2$, $CH_2C\equiv N$, a $(CH_2)_2NH_2$ or $(CH_2)_2Nalk^+X^-$ radical, X halogen and alk alkyl
Y: hydrogen, hydroxyl, halogen or $OSO_3H$,
W: H or OH,
Z: H, $CH_3$.

The compounds of formula (I) have antifungal properties.

15 Claims, No Drawings

DERIVATIVES OF ECHINOCANDINE, THEIR PREPARATION PROCESS AND THEIR USE AS ANTIFUNGALS

PRIOR APPLICATIONS

This application is a division of U.S. patent application Ser. No. 10/018,073 filed Dec. 4, 2001, now U.S. Pat. No. 7,022,669 which is a 371 of PCT/FR00//01568 filed Jun. 8, 2000.

The present invention relates to new derivatives of echinocandine, their preparation process and their use as antifungals.

A subject of the invention is, in all possible isomer forms as well as their mixtures, the compounds of formula (I):

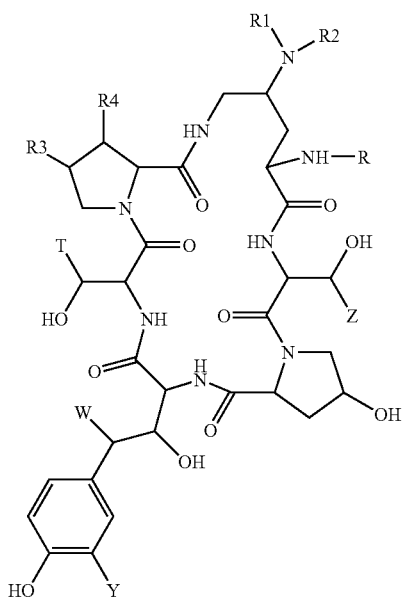

in which
either $R_1$ represents a hydrogen atom or a methyl radical.
$R_2$ represents a cyclohexyl radical substituted by an amine, a $CH_2CH_2NHCH3$ radical, a $CH_2CHCH_3NH_2$ radical, a

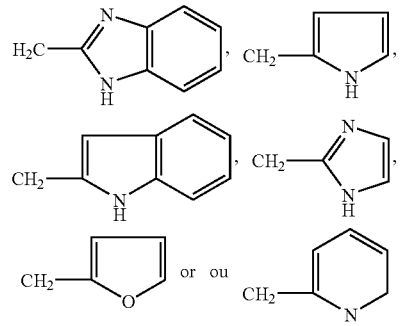

radical, a $CHCH_3CH_2NH_2$ radical, a $—(CH_2)aOH$ radical, a representing an integer comprised between 1 and 8, a $(CH_2)b$-$C\equiv N$ radical, b representing an integer comprised between 1 and 8, a $CHCH_3C_6H_5$ radical, a $(CH_2)—$ $C(CH_3)_2NHCOCF_3$ radical, a $CHCH_3(CH_2)dOH$ radical, d representing an integer comprised between 1 and 8 or $R_1$ and $R_2$ form together with the nitrogen which carries them a ring with 3, 4 or 5 carbons optionally substituted by an amine $R_3$ represents a hydrogen atom, a methyl or hydraxyl radical $R_4$ represents a hydrogen atom or a hydroxyl radical R represents a linear or branched or cyclic chain containing up to 30 carbon atoms, optionally containing one or more heteroatoms, one or more heterocycles or a linear, branched or cyclic acyl radical containing up to 30 carbon atoms optionally containing one or more heteroatoms and/or one or more heterocycles, T represents a hydrogen atom, a methyl radical, a $CH_2CONH_2$ radical, $CH_2C\equiv N$, a $(CH_2)_2NH_2$ or $(CH_2)_2$ $Nalk^+X^-$ radical, X being a halogen atom and alk an alkyl radical containing up to 8 carbon atoms, Y represents a hydrogen atom, a hydroxyl radical or a halogen atom or an $OSO_3H$. radical or one of the salts of this radical, W represents a hydrogen atom or an OH radical, Z represents a hydrogen atom or a methyl radical, as well as the addition salts with acids of the products of formula (I).

Among the addition salts with acids, there can be mentioned those formed with mineral acids, such as hydrochloric, hydrobromic, sulphuric or phosphoric acid or with organic acids such as formic, acetic, trifluoroacetic, propionic, benzoic, maleic, fumaric, succinic, tartaric, citric, oxalic, glyoxylic and aspartic acids, alkanesulphonic acids, such as methane or ethane sulphonic acid, arylsulphonic acids such as benzene or paratoluene sulphonic acids.

Among the preferred compounds of the invention, there can quite particularly be mentioned the compounds of formula I in which T represents a hydrogen atom, those in which W represents a hydrogen atom, those in which Z represents a methyl radical, those in which Y represents a hydrogen atom, those in which $R_3$ represents a methyl radical, those in which $R_4$ represents a hydroxyl radical, and those in which R represents a

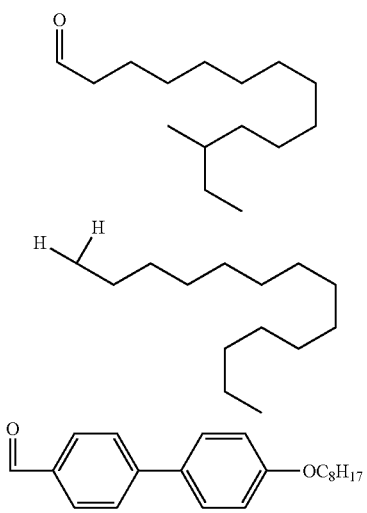

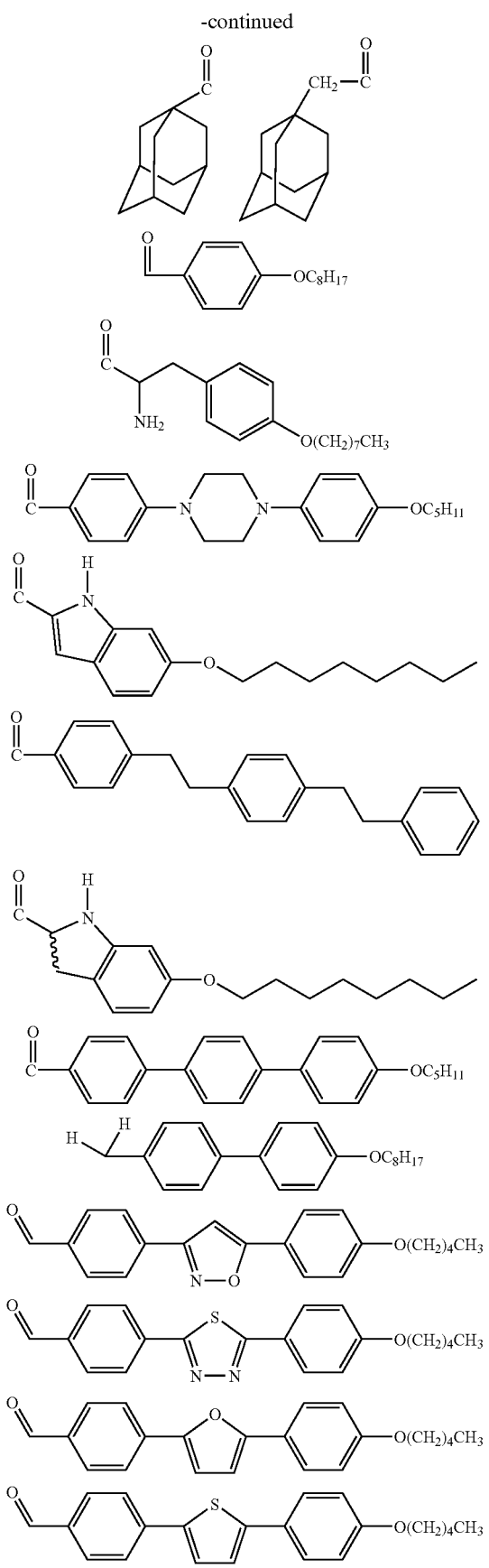
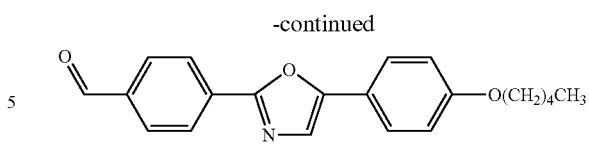
radical.
A most particular subject of the invention is the compounds of formula I in which R represents a
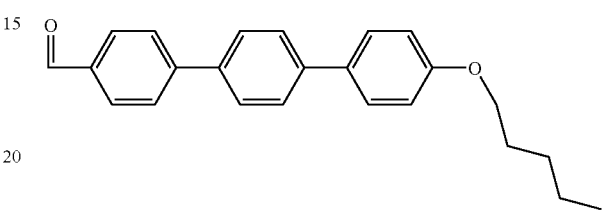
chain or a
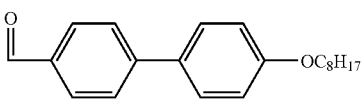
chain.
Among the preferred compounds of the invention, there can be quite particularly mentioned the compounds of formula I in which $R_1$ is a hydrogen atom, those in which $R_2$ is a
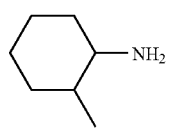
radical,
those in which R2 is a
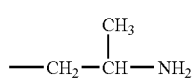
radical, a
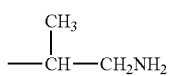

radical or a

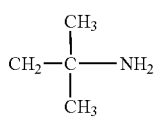

radical or also those in which $R_2$ is a

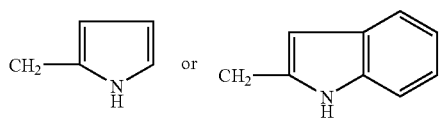

radical

A most particular subject of the invention is the compounds of formula (I), the preparation of which is given hereafter in the experimental part and in particular the products of Examples 2 and 3.

The compounds of formula (I) have useful antifungal properties; they are in particular active on *Candida albicans* and other *Candida* such as *Candida glabrata, krusei, tropicalis, pseudotropicalis, parapsilosis* and *Aspergillus fumigatus, Aspergillus flavus, Cryptococcus neoformans*.

The compounds of formula (I) can be used as medicaments in man or animals, in particular to combat invasive candidosis in the immunosuppressed, digestive, urinary, vaginal or cutaneous candidosis, cryptococcosis, for example neuromeningeal, pulmonary or cutaneous cryptococcosis, bronchopulmonary and pulmonary aspergillosis and invasive aspergillosis in the immunosuppressed.

The compounds of the invention can also be used in the prevention of mycotic illnesses in the congenital or acquired immunosuppressed.

The compounds of the invention are not limited to a pharmaceutical use, they can also be used as fungicides in fields other than the pharmaceutical field.

Therefore a subject of the invention is, as antifungal compounds, the compounds of formula (I) as well as their addition salts with acids.

A subject of the invention is also the compounds of formula (I), as medicaments.

A most particular subject of the invention is the pharmaceutical compositions containing as active ingredient at least one compound of formula (I) or one of its addition salts with pharmaceutically acceptable acids. These compositions can be administrered by oral, rectal, parenteral route or by local route as a topical application on the skin and mucous membranes, but the preferred routes are the oral and parenteral routes.

They can be solid or liquid and can be presented in the pharmaceutical forms commonly used in human medicine, such as for example, plain or sugar-coated tablets, gelatin capsules, granules, suppositories, injectable preparations, ointments, creams, gels; they are prepared according to the usual methods. The active ingredient or ingredients can be incorporated in the excipients usually used in these pharmaceutical compositions, such as talc, gum arabic, lactose, starch, magnesium stearate, cocoa butter, aqueous or non-aqueous vehicles, fatty matter of animal or vegetable origin, paraffin derivatives, glycols, various wetting, dispersing or emulsifying agents, preservatives.

These compositions can also be presented in the form of a powder intended to be dissolved extemporaneously in an appropriate vehicle, for example apyrogenic sterile water.

The dose administered is variable according to the illness treated, the patient in question, the administration route and the product considered. It can be, for example, comprised between 50 mg and 1 g (per day by oral or parenteral route, in adults for the products of Examples 2 and 3.

A subject of the invention is also a preparation process characterized in that a compound of formula (II)

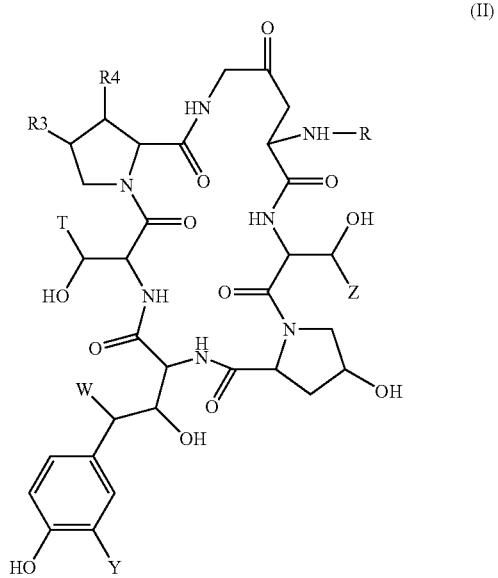

in which R, $R_3$, $R_4$, T, Y, W and Z retain their previous meaning, is subjected to the action of an amine or an amine derivative capable of introducing the

radical in which $R_1$ and $R_2$ retain their previous meaning and if desired is subjected to the action of a reducing agent and/or of an amine functionalization agent, and/or an acid in order to form the salt of the product obtained, and/or a separation agent of the different isomers obtained, and the sought compound of formula (I) is thus obtained.

The compounds of formula (II) described and claimed in the Patent Application WO 99 29716 can be prepared according to a process characterized in that a compound of formula (III)

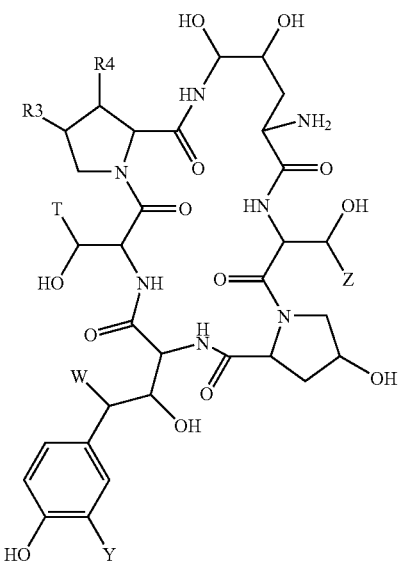

in which the different substituents retain their previous meaning is subjected to the action of an agent capable of replacing NH₂ with NHR, R retaining its previous meaning in order to obtain the compound of formula (IV)

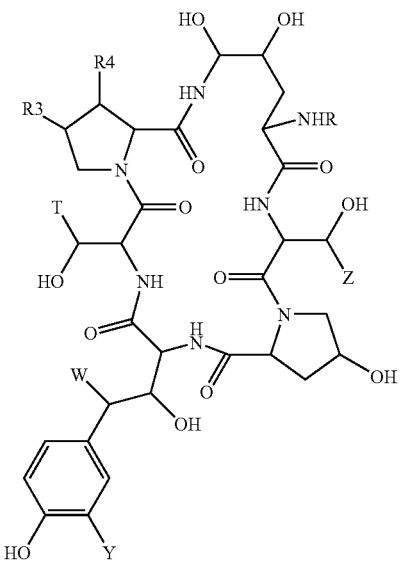

which is subjected to the action of trimethylsilyl iodide in order to obtain the corresponding compound of formula (II) [1,1'-biphenyl]4-carboxylic acid in 22 ml of tetrahydrofuran, followed by agitation for 22 hours at ambient temperature and filtration. The solvents are eliminated under reduced pressure, the residue is taken up in ether, agitated at approximately 35° C., followed by filtration, the solvent is evaporated followed by drying and 1.46 g of expected product is recovered, which is used as it is.

2—Coupling 677 mg of the deoxymulundocandine "nucleus" obtained in Preparation 1 is introduced into 16 ml of DMF. The solution obtained is agitated for 5 minutes and 793 mg of pentafluorophenyl 4'-(octyloxy)-[1,1'-biphenyl]-4-carboxylate obtained above is added. The reaction mixture is maintained under agitation and a nitrogen atmosphere for 24 hours. The reaction mixture is filtered and concentrated. The residue is taken up in ether, triturated, maintained under agitation for 25 minutes, separated, washed with ethyl ether, chromatographed on silica while eluting with a mixture of methylene chloride, methanol, water (86/13/1) then (80/20/1). The sought product is thus obtained. Yield 73%.

Stage B: 1-[N2-[[4'-(octyloxy)-[1,1'-biphenyl]-4-yl]carbonyl]-4-oxo-L-ornithine]-4-[4-(4-hydroxyphenyl)-L-threonine]-5-L-serine-echinocandine B.

311 μl of trimethylsilyl iodide is added to a suspension containing 809 mg of the product of Stage A and 19 ml of acetonitrile. The reaction mixture is maintained under agitation for 15 minutes at 60° C. and under a nitrogen atmosphere. The mixture is poured into a saturated solution of sodium thiosulphate followed by evaporation. The residue obtained is chromatographed on silica, eluting with a methylene chloride/methanol/water mixture 86/13/1. The sought product is obtained. Yield 55%.

Stade C: 1-[4-[((2S)-2-amino-2-methylethyl)amino]-N2-[[4'-(octyloxy)[1,1'-biphenyl]-4-yl]-L-ornithine]-4-[4-(4-hydroxyphenyl)-L-threonine]5-L-serine-echinocandine B trifluoroacetate (isomer A and isomer B).

A solution containing 62.5 mg of (S)-(−)diaminopropane

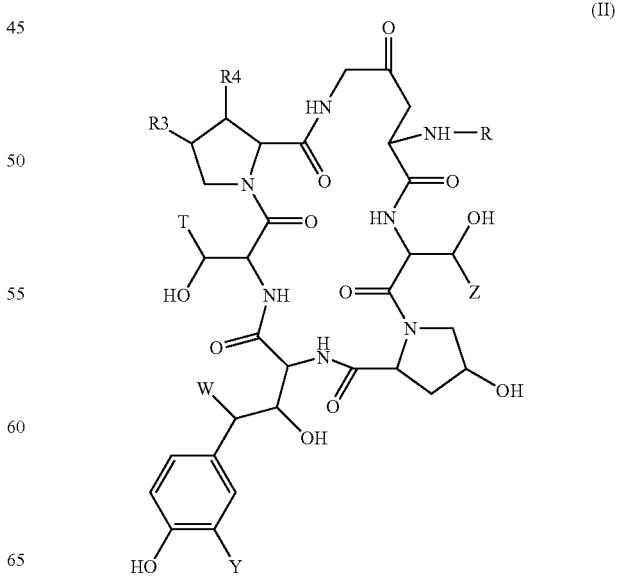

The following examples illustrate the invention without however limiting it.

Preparation 1: "nucleus" of deoxymulundocandine 2 g of deoxymulundocandine is dissolved in 20 ml of DMSO. This solution is poured into a suspension containing 120 g of Actinoplanes utahensis FH2264 in 870 ml of a KH2PO4, K2HPO4 buffer (pH: 6.8). The reaction mixture is maintained under agitation for 70 hours at 30° C. Filtration is carried out. The mycelium is washed with the phosphate buffer (pH: 6.8). The washing liquids and the filtrate are combined. The product obtained is chromatographed on a DIAION Hp 20 resin and a product is obtained which is used as it is hereafter.

EXAMPLE 1

1-[4-[((2S)-2-amino-2-methylethyl)-amino]N2-[[4'-(octyloxy)[1,1'-bipheny l]-4-yl]-carbonyl]-L-ornithine]-4-[4-(4-hydroxyphenyl)-L-threonine]5-L-serine echinocandin B trifluoroacetate (isomer A and isomer B).

Stage A: 1-[(4R,5R)-4,5-dihydroxy-N2-[[4'-(octyloxy)[1,1'-biphenyl]-4-yl]-carbonyl]-L-ornithine]-4-[4(4-hydroxyphenyl)-L-threonine]-5-L-serine echinocandin B.

1—Preparation of the Ester 632 mg of 2,3,4,5,6 pentafluorophenol and 695 mg of N,N'-dicyclohexylcarbodiimide are added to 1 g of 4'-octyloxy-dihydrochloride, 2.25 ml of methanol, triethylamine in order to obtain a pH of 6, a few grains of activated siliporite and 150 mg of the product of the previous stage is agitated for a few minutes at 20° C. 6 mg of NaBH$_3$CN is introduced. Agitation is carried out for 15 hours at 20° C. and after semi-preparative HPLC purification eluent: CH$_3$CN, H$_2$OTFA (50-50-0.02) 11.5 mg, of isomer A, 13 mg of isomer B are obtained.

EXAMPLE 2

1-[4-[[(1H-benzimidazol-2-yl)-methyl)-]-amino]-N2-[[4"-(pentyloxy)[1,1':4',1"-terphenyl]-4-yl]-carbonyl]-L-ornithine]-4-[4-(4-hydroxyphenyl)-L-threonine]-5-L-serine echinocandin B trifluoroacetate (isomer B).

By operating as previously starting, from the nucleus of deoxynmulundecandine prepared in Preparation 1 and obtaining 1-[(4R,5R)-4,5-dihydroxy-N2-[[4"-(pentyloxy)[1, 1':4 ', 1"-terphenyl]-4-yl]carbonyl]-L-threonine]-4-[4-(4-hydroxyphenyl)-L-serine echinocandin B as intermediate product and the corresponding 4-oxo derivative, the sought product was obtained. Isomer A=7.4 mg, isomer B=1.2 mg.

EXAMPLE 3

Trans 1-[4-[(2-aminocyclo-hexyl)-amino]-N2-[[4"-(pentyloxy)[1,1':4',1"-terphenyl]-4-yl]-carbonyl]-L-ornithine]-4-[4(4-hydroxyphenyl)-L-threonine]-5-serine-echinocandin B trifluoroacetate (isomer A).

By operating as previously, starting from 166 mg of the 4-oxo derivative prepared above and 78 mg of (1R,2R)1-2-diaminocyclohexane, 462 mg of crude product is obtained which is chromatographed on silica eluting with a methylene chloride, methanol, H$_2$O, acetic acid mixture 86/13/2/1. 100 mg of product is obtained which is purified by semi-preparative HPLC again with a CH$_3$CN/H$_2$O/TFA mixture=50/50/0.1. 55 mg of isomer A, 5.2 mg of isomer B are obtained.

EXAMPLE 4

1-[4-[(2(S)-aminopropyl)-amino]-N2-[[4"-(pentyloxy)[1,1':4',1"-terphenyl]-4-yl]-carbonyl]-L-ornithine]-4-[4-(4-hydroxyphenyl)-L-threonine]-5-L-serine echinocandin B trifluoracelate (isomer A).

By operating as previously, the sought product was obtained.

EXAMPLE

Pharmaceutical Composition

Tablets were prepared containing:
Product of Example 3 isomer A . . . 150 mg
Excipient s.q.f. . . . 1 g
(Detail of excipient: starch, talc, magnesium stearate).

Pharmacological Study

A—Inhibition of the Glucan Synthase of *Candida albicans*.
*Candida albicans* membranes were purified according to the process described by Tang et al Antimicrob. Agents Chemother 35, 99–103, 1991. 22.5 µg of membrane proteins are incubated in a mixture of 2 Mm of 14C-UDP glucose (specific activity=0.34 mCi./mmol, 50 µg of α-amylase, 1 Mm of dithiotreitol (DTT), 1 Mm EDTA, 100 Mm NaF, 7 µM of GTP-γ-S, 1M of sucrose and 50 Mm of Tris-HCL (pH 7.8) in a volume of 100 µl. The medium is incubated at 25° C. for 1 hour and the reaction is terminated by adding TCA at a final concentration of 5%. The reaction mixture is transferred onto a pre-humidified glass fibre filter. The filter is washed, dried and its radioactivity is counted.
Mulundocandine is used as a positive control.
Control of the vehicle is carried out with the same quantity of 1% DMSO. The results obtained show that in this test the products of the invention show a good activity in particular the products of Example 3 isomer A.

B—Activity on the *Aspergillus fumigatus* Enzyme.
The enzyme is prepared according to the process of Beaulieu et al.(Antimicrob. Agents Chenother 38, 937–944, 1994.
The protocol used is identical to the protocol described above for the enzyme of Candida albicans except that dithiotreitol is not used in the reaction-mixture.
In this test the products show a good activity.

The invention claimed is:

1. A compound selected from the group consisting of all possible stereoisomers of a compound of the formula

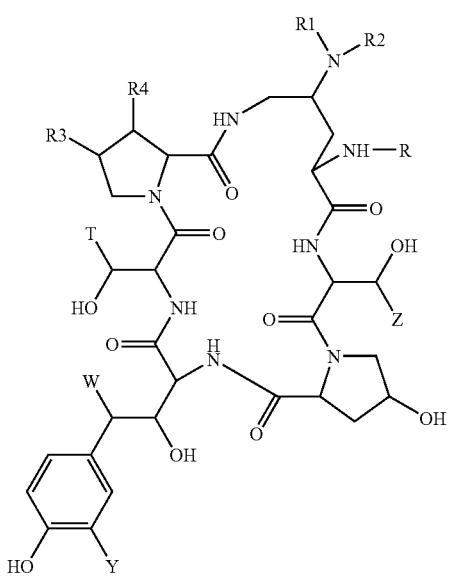

I wherein $R_1$ is hydrogen or methyl, $R_2$ is cyclohexyl substituted with an amine, $R_3$ is selected from the group consisting of hydrogen, methyl and hydroxyl, $R_4$ is hydrogen or hydroxyl, R is selected from the group consisting of a) alkyl and cycloalkyl of up to 30 carbon atoms optionally containing at least one heteroatom or at least one heterocycle, and b) acyl or cyclic acyl of up to 30 carbon atoms optionally containing at least one heteroatom or at least one heterocycle, T is selected from the group consisting of hydrogen, methyl, —$CH_2CONH_2$, —$CH_2$—C≡N, and —$(CH_2)_2NH_2$, Y is selected from the group consisting of hydrogen, hydroxyl, halogen and —$OSO_3H$ or a salt thereof, W is hydrogen or OH, Z is hydrogen or methyl; and a non-toxic, pharmaceutically acceptable acid addition salt thereof.

2. The compound of claim 1 in which T is hydrogen.
3. The compound of claim 1 in which W is hydrogen.
4. The compound of claim 1 in which Z is methyl.
5. The compound of claim 1 in which Y is hydrogen.
6. The compound of claim 1 in which $R_3$ is methyl.
7. The compound of claim 1 in which $R_4$ is hydroxyl.
8. The compound of claim 1 in which R is selected from the group consisting of

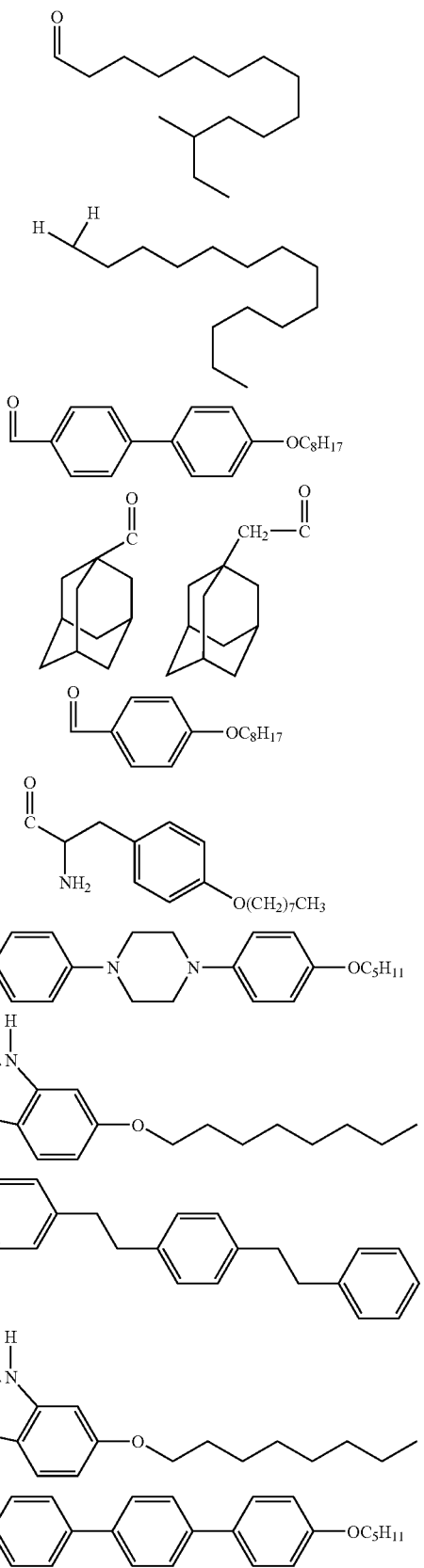

-continued

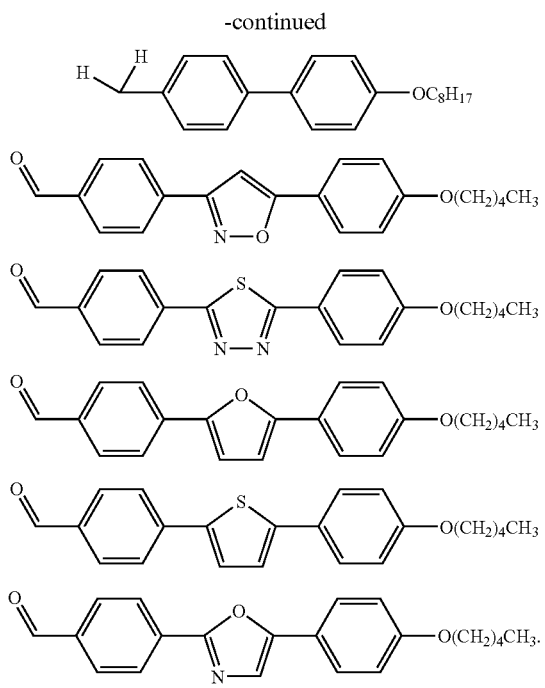

9. The compound of claim 8 in which R is

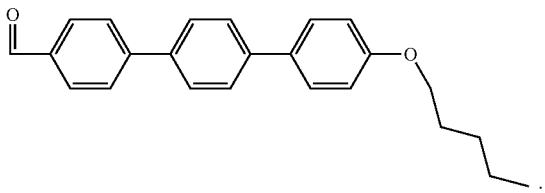

10. The compound of claim 8 in which R is

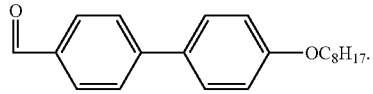

11. The compound of claim 1 in which $R_1$ is hydrogen.

12. The compound of claim 1 in which $R_2$ is

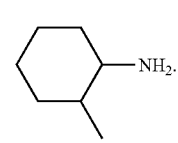

13. The compound of claim 1 is trans 1-[4-[(2-aminocyclo-hexyl)-amino]N2-[[4"(pentyloxy)[1,1':4', 1"-terphenyl]-4-yl-carbonyl]-L-ornithine]-4-[4(4-hydroxyphenyl)-L-threonine]-5-L-serine-echinocandine B trifluoroacetate (isomer A).

14. An antifungal composition comprising an antifungally effective amount of the compound of claim 13 and an inert pharmaceutical carrier.

15. A method of treating fungal infections in warm-blooded animals comprising administering to warm-blooded animals in need thereof an antifungally effective amount of the compound of claim 13.

* * * * *